United States Patent [19]

Easson, Jr. et al.

[11] Patent Number: 4,948,733
[45] Date of Patent: Aug. 14, 1990

[54] ZOOGLOEA TRANSFORMATION USING EXOPOLY SACCHARIDE NON-CAPSULE PRODUCING STRAINS

[75] Inventors: Donald D. Easson, Jr., Cambridge; Oliver P. Peoples, Arlington; Anthony J. Sinskey, Boston, all of Mass.

[73] Assignee: Massachusetts Institute of Technology, Cambridge, Mass.

[21] Appl. No.: 35,604

[22] Filed: Apr. 7, 1987

Related U.S. Application Data

[63] Continuation-in-part of Ser. No. 891,136, Jul. 28, 1986, abandoned.

[51] Int. Cl.$^5$ .................. C12N 15/64; C12N 1/20; C12N 1/21; C12N 15/01; C12P 19/04
[52] U.S. Cl. .................. 435/172.3; 435/252.1; 435/256.3; 435/172.1; 435/320; 435/101; 935/55; 935/56; 935/58; 935/60; 935/72
[58] Field of Search ............ 435/101, 102, 103, 104, 435/172.3, 253, 317, 91, 71, 172.1, 252.1, 252.3, 320; 935/55, 56, 58, 72, 60

[56] References Cited

U.S. PATENT DOCUMENTS

| | | | |
|---|---|---|---|
| 3,314,801 | 4/1967 | Cadmus et al. | 536/123 |
| 3,406,114 | 10/1968 | Goren et al. | 435/101 |
| 3,632,570 | 1/1972 | Gill | 536/123 |
| 3,923,782 | 12/1975 | Finn et al. | 536/123 |
| 4,329,448 | 5/1982 | Cox et al. | 252/8.555 |
| 4,394,447 | 7/1983 | Cadmus et al. | 435/104 |
| 4,508,823 | 4/1985 | Olsen | 435/172.3 |
| 4,529,797 | 7/1985 | Peik et al. | 536/123 |
| 4,567,140 | 1/1986 | Voelskow et al. | 435/42 |
| 4,575,551 | 3/1986 | Fujiyama et al. | 536/123 |
| 4,626,504 | 12/1986 | Puhler et al. | 435/172.3 |
| 4,638,059 | 1/1987 | Sutherland | 538/121 |
| 4,647,657 | 3/1987 | Wan | 536/123 |
| 4,713,449 | 12/1987 | Vanderslice et al. | 536/123 |
| 4,752,580 | 6/1988 | Downs | 435/104 |
| 4,758,356 | 7/1988 | Downs | 252/8.51 |

OTHER PUBLICATIONS

Norberg et al., Applied and Envir. Microbiol., vol. 44, pp. 1231–1237 (1982).
Harding et al., Abstracts, ASM 1986, 0–64.
Darzins et al., J. of Backsiol., vol. 159, pp. 9–18 (1984).
Ditta et al., Proc. Natl. Acad. Sci., 77(12), 7347–7351, (Dec. 1980).
Farrah et al., Applied and Environ. Microbiol., 32(1), 33–37, (Jul. 1976).
Ish-Horowicz, Nucleic Acids Researach, 9(13), 299–2998, (Jul. 10, 1981).
Okita et al., Structural Genes of Bacterial Glycogen Biosynthesis, 256, 6944–6952, (1981).
Parsons et al., Applied Microbiology, 21(4), 657–661, (Apr. 1971).
Sinskey et al., Biotechnology in Food Processing, (1986).
Stauffer et al., J. Food Sci., 45 746–952, (1980).

Primary Examiner—Robin L. Teskin
Assistant Examiner—Larry Millstein
Attorney, Agent, or Firm—Kilpatrick & Cody

[57] ABSTRACT

Two new bacterial strains designated Zoogloea ramigera 115SL and Zoogloea ramigera 115SLR, a rifampicin resistant derivative of 115SL, have been developed. These strains are derived from the wild type Zoogloea ramigera 115, ATCC 25935. The two new strains produce a novel exopolysaccharide (EPS) and have several desirable characteristics that are absent from the parent strain, including improved culture properties, since they do not produce an EPS capsule layer like that of the parent 115 strain. The 115SL EPS is instead excreted as a slime layer which is not confined to the immediate area surrounding the cells. Since cells are not trapped within a floc where they grow at a reduced rate or die because of nutrient starvation, the new strains have more consistent and reproducible growth cycles and increased growth rates. As a consequence, exopolysaccharide production is more consistent and titers are higher. The separation of the EPS from the cells is also much easier and more economical. The other very important characteristic of strains 115SL and 115SLR is that they are able to receive foreign DNA using conventional techniques due to the absence of the capsule layer. This facilitates the application of recombinant DNA technology to control and produce novel exopolysaccharides.

12 Claims, 3 Drawing Sheets

ZOOGLOEA TRANSFORMATION USING EXOPOLY SACCHARIDE NON-CAPSULE PRODUCING STRAINS

BACKGROUND OF THE INVENTION

This application is a continuation-in-part application of U.S. Ser. No. 891,136 filed Jul. 28, 1986, by Anthony J. Sinskey, Donald Davidson Easson Jr., Oliver P. Peoples and Chokyun Rha entitled "Method to Control and Produce Novel Biopolymers". now abandoned in favor of pending continuation application U.S. Ser. No. 07/329,594 filed Mar. 28, 1989.

The present invention is in the field of genetically engineered organisms, particularly genetically modified exopolysaccharide producing strains of *Zoogloea ramigera*.

Polysaccharide biopolymers have found applications in many industries, including the food, cosmetic, chemical, biomedical, waste treatment and oil industries.

Flocculation is one important commercial use of biopolymers. Several types of floc-forming bacteria have been identified. The most efficient are the cellulose, or cellulose-like, producing bacteria such as certain species of Pseudomonas, Aerobacter, Agrobacterium, Azotobacter and Zoogloea. Flocculation of these bacteria appears to occur when cells become embedded in a network of exopolysaccharide fibrils. Other floc-forming bacteria produce capsular polysaccharides enclosing large packets of cells which lead to floc formation. An example of this phenomenon occurs with *Zoogloea ramigera* 115. In some cases these exocellular polysaccharides have metal ion binding properties.

*Z. ramigera* 115, designated ATCC 25935 by the American Type Culture Collection, Rockville, Md., is an exopolysaccharide matrix forming strain which, when grown in a nitrogen limiting medium, converts 60% (w/w) of the available glucose substrate into a water soluble capsular branched heteropolysaccharide composed of glucose and galactose in a molar ratio of 2:1 with approximately 3% to 5% pyruvate. The negatively charged carboxyl groups of the pyruvate are thought to be primarily responsible for the biopolymer's high affinity for heavy metal ions.

Due to the unique rheological and strong metal binding properties of the *Zoogloea ramigera* exocellular polysaccharide, it is desirable to isolate, characterize, express and modify the exopolysaccharide genes produced by *Zoogloea ramigera* strains. It is also desirable to provide the genes or complementary nucleotide sequences for production of exocellular polysaccharides produced by *Zoogloea ramigera* for use in synthesis of novel polysaccharides.

It is therefore an object of the present invention to provide nucleotide sequences which can be used to produce novel biopolymers, especially the *Zoogloea ramigera* exopolysaccharides.

It is still further object of the present invention to produce a system for production of biopolymers with enhanced rate and level of synthesis and greater ease in isolation of the biopolymers.

SUMMARY OF THE INVENTION

Two new bacterial strains designated *Zoogloea ramigera* 115SL and *Zoogloea ramigera* 115SLR have been developed. They have been designated ATCC 53589 and ATCC 53590, respectively, as deposited on Mar. 5, 1987 with the American Type Culture Collection in Rockville Md. Strain 115SLR is a rifampicin resistant derivative of 115SL. These strains are derived from the wild type *Zoogloea ramigera* 115, ATCC 25935. The two new strains produce a novel exopolysaccharide (EPS) and have several desirable characteristics that are absent from the parent strain.

The new strains, 115SL and 115SLR, have improved culture properties, as compared to the parent 115 strain, since they do not produce an EPS capsule layer like that of strain 115. The 115SL EPS is excreted as a slime layer which is not confined to the immediate area surrounding the cells. The result is that strains 115SL and 115SLR do not flocculate during growth, unlike 115 which forms large cell flocs during the growth phase. Since cells are not trapped within a floc where they grow at a reduced rate or die because of nutrient starvation, the new strains have the advantage of more consistent and reproducible growth cycles and increased growth rates.

As a consequence of the higher cell density and healthier cultures, exopolysaccharide production is more consistent and titers are higher. The separation of the EPS from the cells is also much easier and more economical.

In contrast to strain 115, a very important characteristic of strains 115SL and 115SLR is that they are able to receive foreign DNA using conventional techniques such as by conjugation, due to the absence of the capsule layer. This facilitates the application of recombinant DNA technology to control and produce novel expolysaccharides.

Compositional analysis of the exopolysaccharide produced by 115SL and 115SLR demonstrates that there are no differences between their EPS and the EPS of strain 115 with respect to monosaccharide composition. However, there is an increase of about 30 to 50% in the pyruvate content in the EPS from 115SL and 115SLR.

DETAILED DESCRIPTION OF THE INVENTION

Isolation of new *Z. ramigera* strains *115*SL and *115*SLR and identification of their genes for polysaccharide synthesis enable development of strategies for the manipulation and control of the biosynthetic pathway for exopolysaccharide production at the genetic level. Strategies for controlled polymer production and structure include: placing the polysaccharide biosynthetic genes under the control of regulatable promoters; the introduction of these genes into new host stains to enable the development of more economic processes for polysaccharide production; mutagenesis of the genes to alter the enzyme activities and the resulting polymer structure; and the construction of novel pathways for polysaccharide synthesis by "mixing" genes from different strains of Z. ramigera or other organisms.

Figure 1:
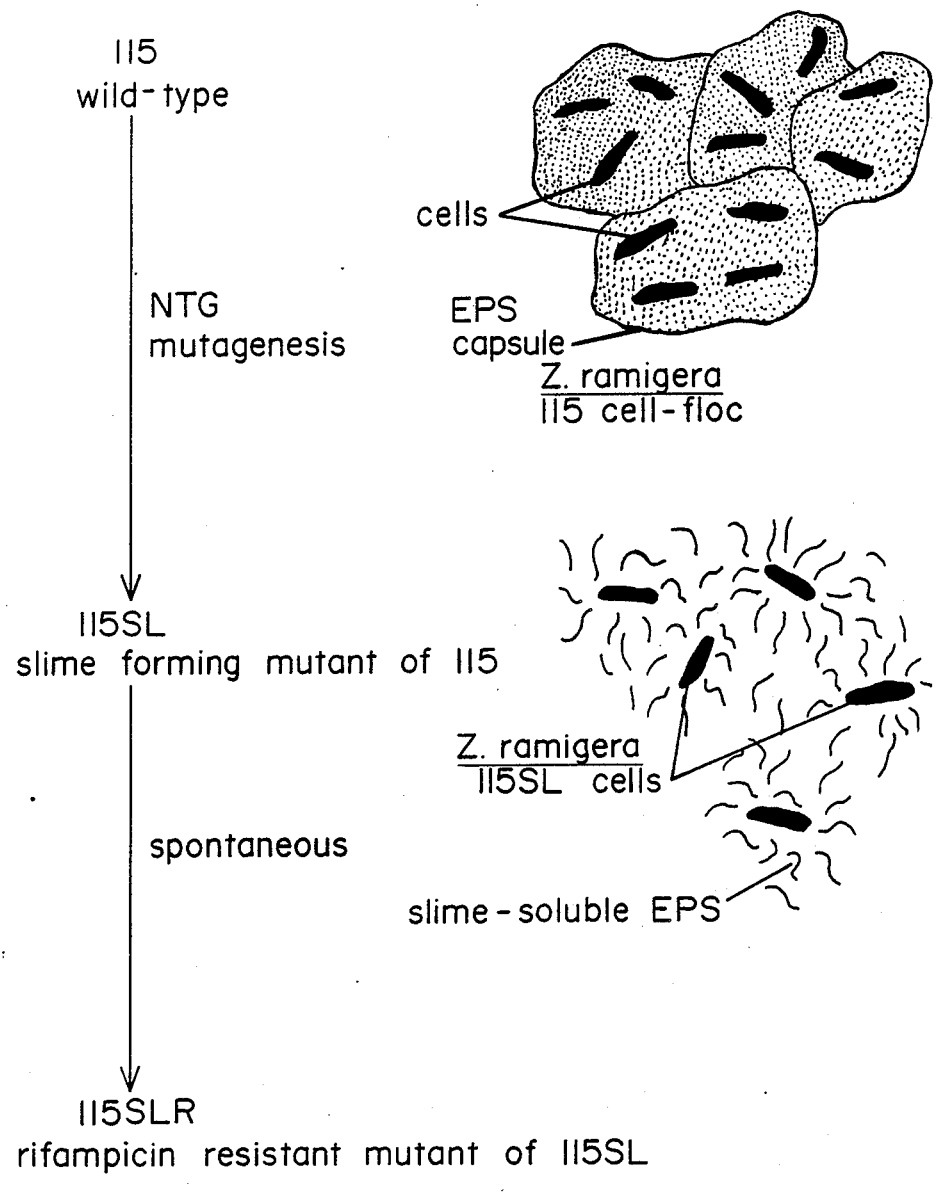
FIG. 1 is a schematic diagram of the derivation of *Z. ramigera* strains 115SL and 115SLR.

The novel Z. ramigera strains were derived from Z. ramigera 115 (ATCC 25935) obtained from the American Type Culture Collection Rockville, Maryland, as shown in FIG. 1. The Z. ramigera 115 strain was mutated by addition of 40 micrograms nitrosoguanidine (NTG)/ml of cells followed by incubation without shaking at 30° C. Samples were treated for between zero and 60 minutes to establish a kill curve (concentration of cells decreased from $1 \times 10^7$ at zero minutes to $6.4 \times 10^5$ at 60 minutes). The cells that were treated for twenty minutes (surviving concentration equal to $6 \times 10^6$ cells) to thirty minutes (surviving concentration equal to $4 \times 10^6$ cells) were then plated out. Cells were screened on plates containing Cellufluor for loss of fluorescence, indicating loss of polysaccharide production, and a change in morpholopy.

The Zoogloea ramigera strains were characterized by microscopy, morphological characterization and determination of the ability to grow and produce polysaccharide on different mediums. A complex medium and a defined medium were selected that contain all the requirements for growth and polysaccharide production and detection.

The media and culture conditions are as follows: Z. ramigera cultures are stored frozen at $-70°$ C. in trypticase soy broth (TSB) medium containing 7% DMSO and 15% glycerol. The various Z. ramigera strains are routinely cultured in either the TSB medium or a defined medium, described by Norberg and Enfors in Appl. Env. Microbiol. 44, 1231–1237 (1982) having the following composition: 25 g glucose, 2 g $K_2HPO_4$, 1 g $KH_2PO_4$, 1 g $NH_4Cl$; 0.2 g $MgSO_4 7H_2O$; 0.01 g yeast extract (Difco Laboratories) in one liter distilled water, where the glucose, $MgSO_4 7H_2O$, yeast extract and salts are autoclaved separately. 100 ml cultures of Z. ramigera are grown on a rotary shaker (200 rpm) at 30° C. in 500 ml baffled shake flasks for periods up to two weeks.

Figure 2:
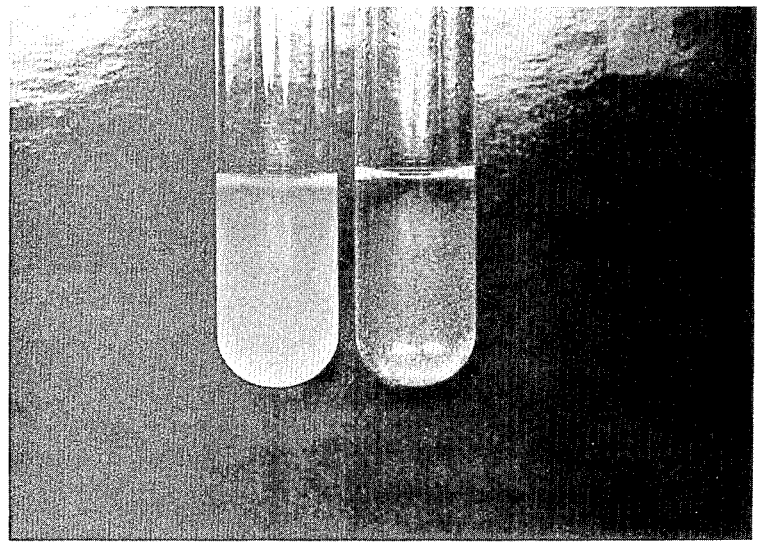
FIG. 2 is a photo of *Z. ramigera* 115 (right) and *Z. ramigera* 115 SL (left), demonstrating the floc-forming characteristic of strain 115 and its absence in strain 115SL which produces a turbid or non-flocculated culture.

Cellufluor (Polysciences Chemicals, Warrington, Pa.) is a fluorescent dye, disodium salt of 4,4'-bis-[4-anilino-bis-diethyl-amino-S-triazin-2-ylamin]- 2,2'-stilbene-disulfonic acid, that binds specifically to beta (1–3) and beta (1–4) glycosyl linkages and fluoresces when exposed to UV light. Cellufluor is added to agar plates, pH 7.4, at a concentration of 200 micrograms/ml and used to determine polysaccharide production in Z. ramigera. Strain 115 flocculates and has a discernable polysaccharide capsule layer surrounding the cell flocs, as shown in FIG. 2, as well as a very unique colonial morphology. As shown in FIG. 1, the change in appearance is striking. The 115SL and 115SLR strains of Z. ramigera do not flocculate.

115SLR is a spontaneous rifampicin resistant mutant of 115SL and is particularly useful in selection processes during genetic manipulations. For example, it can be used to select against donor strains in experiments involving the conjugal transfer of plasmids and plasmid-/gene libraries.

Southern hybridization of $^{32}$P-pHP27, a 115/pLAFR3 recombinant plasmid that causes a change in the morphology of Z. ramigera I-16-M, was used to confirm that 115SL is derived from 115.

The 115 polymer is purified by the addition of concentrated NaOH to the cell culture at a final concentration of 0.2M, followed by the addition of 3 volumes of ethanol to precipitate the polymer and other materials. The precipitate is collected and redissolved in half the original volume of water. Protein is removed by either extracting twice with phenol or by ultrafiltration. The aqueous phase is dialyzed, lyophilized and ground to yield a fine white powder.

Since it is not cell-bound, the exopolysaccharide produced by 115SL and 115SLR is purified without using the alkali treatment or the phenol extraction. Not only is the purification process thereby simplified, it does not remove alkali-labile acetyl moieties from the purified 115SL and 115SLR exopolysaccharide. Since all previously used purification procedures have included an alkali step, this is believed to be the first time the exopolysaccharide has been available in purifed form with acetate groups present on the polymer.

Total carbohydrate concentration in culture broths and polymer solutions is determined by the phenol reaction, described by Gerhardt in Manual of Methods for General Bacteriol. (Washington Amer. Soc. Microbiol. 1981). Glucose, galactose and Xanthan gum (Sigma Chemical Co., St. Louis, Mo.) are used as standards. Total protein concentration in culture broths and polymer solutions is determined using the Bio-Rad protein assay (Bio-Rad Laboratories, Richmond, Calif., 1979). Lysozyme is used as the standard. Cellular protein is released by boiling in 0.2N NaOH.

Purified polysaccharide is hydrolyzed in 1M trifluoroacetic acid at 120° C. for times varying between 30 minutes and 2 hours. Monosaccharides in the polysaccharide hydrolysate are separated using a Waters HPLC equipped with a Brownlee Polypore PB, lead loaded cation exchange column, operated at 85° C., with water as the eluent. Detection is by refractive index using a Waters Model 401 Differential Refractometer. The polysaccharide can further characterized by proton NMR spectroscopy and infared spectroscopy. Infrared analysis, along with the monosaccharide composition data, can be compared to the composition and IR scans of polysaccharides from mutant or genetically manipulated strains to detect changes in structure.

The polymer produced by Zoogloea ramigera 115SL consists of glucose and galactose in a ratio of approximately 2:1, the same as the exopolysaccharide produced by strain 115. The pyruvate content is slightly higher in the 115SL and 115SLR strains, however, by approximately 30 to 50%.

The isolated exopolysaccharide produced by Z. ramigera 115 SL and 115 SLR has a number of uses similar to that of the exopolysaccharide isolated for the parent strain. For example, the polymer can be used as a flocculant, in the isolation and removal of heavy metal ions, and as a viscosity modifying agent. However, although similar to the 115 exopolysaccharide, some differences in application are expected due to the slightly higher pyruvate level and the presence of the acetate moiety.

Figure 3A:
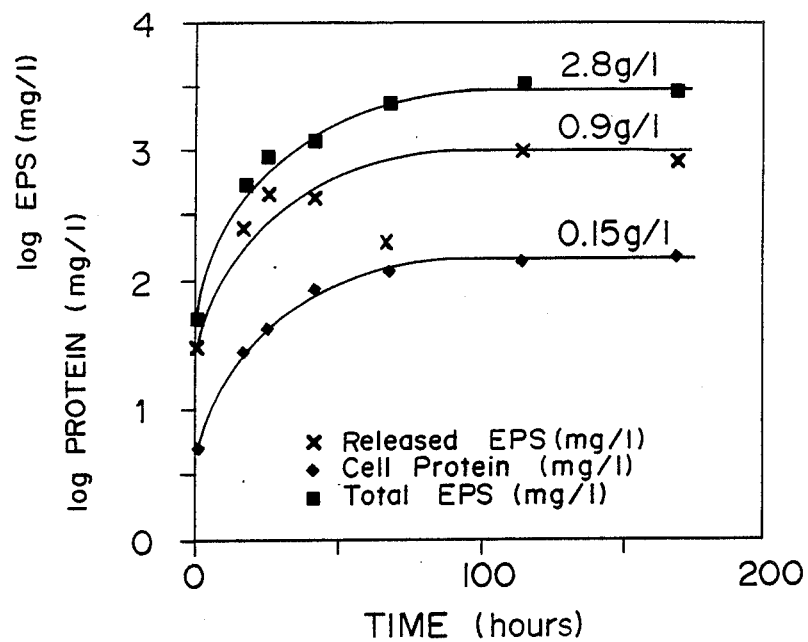
FIGS. 3A and B are graphs of the growth (measured as mg protein/l) and exopolysaccharide production, measured as mg exopolysaccharide/l released into the supernatant and the total mg exopolysaccharide/l produced, of *Z. ramigera* 115 (A) and *Z. ramigera* 115SL (B).
Figure 3B:
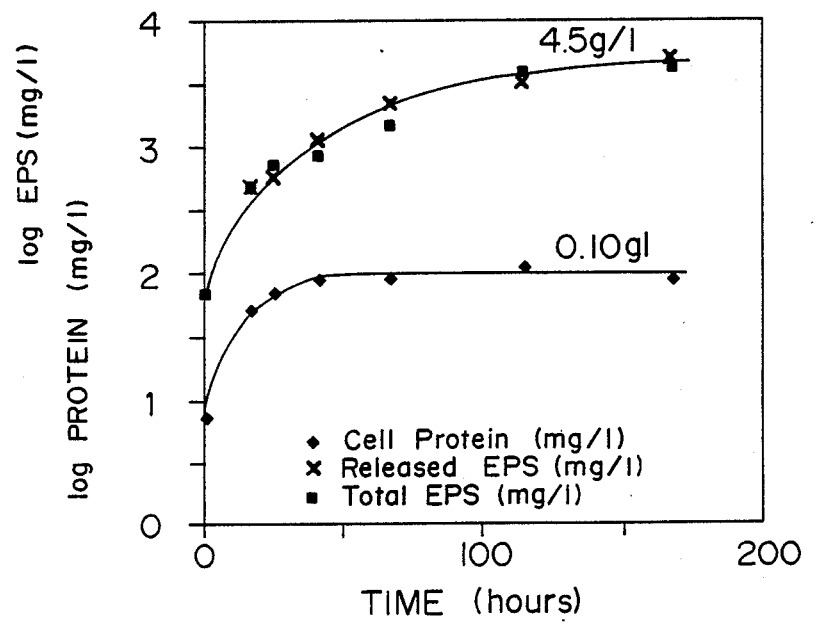

The new strains, 115SL and 115SLR, are useful in ways that the parent strain 115 is not. For example, it produces higher, more consistent levels of polysaccharide which is more easier purified since the cell floc present in 115 is absent. The number of cells which can be grown in culture is also greater due to the easier diffusion of nutrients into the cell. The differences in cell growth and polymer production are demonstrated in FIGS. 3A and 3B. The total amount of EPS (mg/l) produced, as well as the total amount released into the medium over time as a percentage of the total EPS produced (mg/l), for 115 (FIG. 3A) is significantly less than that for 115SL (FIG. 3B). The initial growth curve for 115SL (FIG. 3B), shown by the total protein, is also much sharper than it is for 115 (FIG. 3B).

The primary advantage of the new 115SL and 115SLR strains, however, is that they can be more easily manipulated genetically. As demonstrated below, the 115SL and 115SLR strains can accept foreign or plasmid DNA in a relatively high yield by conjugal transfer without extensive manipulation. This allows not only the isolation, characterization and modification of the genes for exopolysaccharide production but also the insertion of genes encoding additional enzymes for synthesis of biopolymers. Methods for manipulation and construction of pathways for polymer synthesis are described in detail in co-pending application. U.S. Ser. No. 07/3429,594 filed Mar. 28, 1989, now abandoned.

As an example of the application of these methods to *Z. ramigera* 115SL and 115SLR, transposon mutants of *Z. ramigera* 115SL were constructed by the method described in pending, U.S. Ser. No. 07/329,594 filed Mar. 28, 1989, now abandoned and screened for changes in exopolysaccharide composition and production, which describes the transfer of a Tn5 containing derivative of pRK 2013 in *Z. ramigera* strains using *E. coli* MM294A by conventional techniques for conjugation. Several Tn5 mutants that were non-fluorescent on Cellufluor were recovered. Although not adsorbing Cellufluor, the mutants are producing exopolysaccharide. These polymers have apparently undergone a structural or compositional change from that of the original exopolysaccharide.

A pLAFR3/115 gene library was then introduced into these mutants. The resulting transconjugants were screened for fluorescence on Cellufluor and for changes in colony morphology. One class of complemented strains regained the ability to fluoresce on Cellufluor. A second class of complemented strains had colony morphology identical to that of the wild-type 115.

Modifications and variations of the present invention, a method and means for producing genetically manipulated biopolymers including the exopolysaccharides produced by *Zoogloea ramigera* strains, will be obvious to those skilled in the art from the foregoing detailed description. Such modifications and variations are intended to come within the scope of the following claims.

We claim:

1. A method for introducing foreign DNA into Zoogloea comprising:
   providing isolated nucleotide sequences,
   inserting said isolated sequences into a vector capable of replicating in Zoogloea; and
   introducing said vector containing said isolated sequences into an exopolysaccharide producing, non-capsule forming *Zoogloea ramigera* strain.

2. The method of claim 1 wherein said sequences are inserted into said *Zoogloea ramigera* by conjugation.

3. The method of claim 1 wherein said *Zoogloea ramigera* strain is ATCC 53589, or a derivative thereof.

4. The method of claim 1 wherein said *Zooglea ramigera* strain is ATCC 53590, or a derivative thereof.

5. The method of claim 1 further comprising mutating capsule-forming *Zoogloea ramigera* to form the exopolysaccharide, non-capsule producing *Zoogloea ramigera*.

6. *Zoogloea ramigera* 115SL ATCC 53589.

7. *Zoogloea ramigera* 115SLR ATCC 53590.

8. The *Zoogloea ramigera* of claim 6 further comprising a vector capable of replication in Zoogloea.

9. The *Zoogloea ramigera* of claim 7 further comprising a vector capable of replication in Zoogloea.

10. A method for making a *Zoogloea ramigera* strain comprising mutating capsule-forming *Zoogloea ramigera*.

11. The method for making an exopolysaccharide, non-capsule producing *Zoogloea ramigera* strain of claim 10 wherein the Zoogloea is mutated using a chemical mutagen.

12. An isolated exopolysaccharide, non-capsule producing *Zoogloea ramigera* produced by mutation of a capsule forming *Zoogloea ramigera* strain.

* * * * *